US009987456B2

(12) United States Patent
Lee et al.

(10) Patent No.: US 9,987,456 B2
(45) Date of Patent: Jun. 5, 2018

(54) HUMIDIFYING DEVICE FOR BREATHING MASK

(71) Applicant: DELTA ELECTRONICS, INC., Taoyuan County (TW)

(72) Inventors: Kuo-Liang Lee, Taoyuan County (TW); Rung-Yung Lin, Taoyuan County (TW); Sheng-Wen Pai, Taoyuan County (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 603 days.

(21) Appl. No.: 14/662,289

(22) Filed: Mar. 19, 2015

(65) Prior Publication Data

US 2016/0101257 A1    Apr. 14, 2016

(30) Foreign Application Priority Data

Oct. 9, 2014 (TW) .............................. 103135123 A (51) Int. Cl.
*A61M 16/10* (2006.01)
*A61M 16/00* (2006.01)
(Continued)

(52) U.S. Cl.
CPC ...... *A61M 16/164* (2014.02); *A61M 16/1045* (2013.01); *A61M 16/0003* (2014.02);
(Continued)

(58) Field of Classification Search
CPC .......... A61M 16/0875; A61M 16/1045; A61M 16/109; A61M 16/1095; A61M 16/14;
(Continued)

(56) References Cited

U.S. PATENT DOCUMENTS 1,117,612 A * 11/1914 Thompson ............. A01G 27/00
239/38
4,038,980 A * 8/1977 Fodor ............... A61M 16/1075
128/203.27

(Continued)

OTHER PUBLICATIONS

Office Action dated Jun. 23, 2017 from corresponding application No. CN 201410529667.0.

*Primary Examiner* — (Jackie) Tan-Uyen T Ho
*Assistant Examiner* — Joseph D Boecker
(74) *Attorney, Agent, or Firm* — Hauptman Ham, LLP (57) ABSTRACT

The present invention relates to a humidifying device for a breathing mask. The breathing mask includes a breathing tube assembled thereto. The humidifying device includes a body, a liquid discharger, a liquid receiver, and a water-absorbent member. The body is connected to the breathing tube. The body includes a passage communicating with the breathing tube. The liquid discharger is fixed to the body. The liquid discharger includes a liquid outlet communicating with the passage. The liquid receiver is fixed to the body and is disposed below the liquid discharger. The liquid receiver includes a liquid inlet communicating with the passage. The water-absorbent member consists of a filtering material. The water-absorbent member is accommodated in the passage and disposed between the liquid outlet and the liquid inlet.

23 Claims, 5 Drawing Sheets

(51) Int. Cl.
*A61M 16/06* (2006.01)
*A61M 16/08* (2006.01)
*A61M 16/16* (2006.01)
*A61M 16/20* (2006.01)

(52) U.S. Cl.
CPC ......... *A61M 16/06* (2013.01); *A61M 16/0875* (2013.01); *A61M 16/109* (2014.02); *A61M 16/161* (2014.02); *A61M 16/202* (2014.02); *A61M 2205/3368* (2013.01)

(58) Field of Classification Search
CPC .. A61M 16/142; A61M 16/147; A61M 16/16; A61M 16/161; A61M 16/00; A61M 16/0003; A61M 16/0057; A61M 16/0066; A61M 16/06; A61M 16/0816; A61M 16/164; A61M 16/201; A61M 2205/3368
USPC .................................................. 261/103, 106
See application file for complete search history.

(56) References Cited

U.S. PATENT DOCUMENTS

| | | | |
|---|---|---|---|
| 4,288,396 A * | 9/1981 | Ottestad | A61M 16/16 128/203.27 |
| 5,255,674 A | 10/1993 | Oftedal et al. | |
| 5,407,604 A * | 4/1995 | Luffman | B01F 3/0407 210/94 |
| 6,155,255 A | 12/2000 | Lambert | |
| 9,816,715 B2 * | 11/2017 | Morikawa | F24F 6/02 |
| 2004/0254524 A1 * | 12/2004 | Spearman | A61M 13/003 604/26 |
| 2005/0133942 A1 * | 6/2005 | Schuld | F24F 6/043 261/106 |
| 2006/0081247 A1 * | 4/2006 | Britt | A61M 16/16 128/203.16 |
| 2009/0126735 A1 * | 5/2009 | Nitta | A61M 16/1075 128/203.26 |
| 2010/0200398 A1 * | 8/2010 | Thiruppathi | C02F 1/4618 204/274 |
| 2010/0206308 A1 * | 8/2010 | Klasek | A61M 16/0066 128/203.27 |
| 2013/0220322 A1 * | 8/2013 | Ruff | A61M 16/16 128/203.26 |
| 2014/0158128 A1 * | 6/2014 | Heimel | A61M 16/109 128/203.26 |
| 2015/0209528 A1 * | 7/2015 | Lee | A61M 11/02 128/200.23 |

* cited by examiner

HUMIDIFYING DEVICE FOR BREATHING MASK

BACKGROUND

1. Technical Field

The present invention relates to a humidifying device and, in particular, to a humidifying device for a breathing mask.

2. Related Art

Breathing masks in the market are mainly used to cover over the mouth and nose of a patient, so as to isolate the mouth and nose from the outside environment. A breathing tube is assembled on the breathing mask. Outside oxygen or therapeutic gas is conveyed into the breathing mask through the breathing tube, so as to provide the oxygen or therapeutic gas to the patient for breathing.

In order to enhance breathing comfort for patients, a breathing tube usually includes a humidifying device to increase humidity of the oxygen or therapeutic gas, thereby preventing breathing discomfort such as thirst.

However, the aforesaid humidifying device has the following defects. First, the conventional humidifying device is too big to carry on. Second, the water tank in the humidifying device contains a great amount of water to be heated, so more power is required to heat the great amount of water to achieve a humidifying effect.

In view of the foregoing, the inventor made various studies to improve the above-mentioned problems to realize the improvements, on the basis of which the present invention is accomplished.

BRIEF SUMMARY

It is an object of the present invention to provide a humidifying device for a breathing mask, which is constituted by simple parts assembled to one another, thereby reducing the size of the humidifying device and saving power.

Accordingly, the present invention provides a humidifying device for a breathing mask. The breathing mask including a breathing tube assembled thereto. The humidifying device comprises: a body connected to the breathing tube, the body including a passage communicating with the breathing tube; a liquid discharger including a liquid outlet communicating with the passage; a liquid receiver including a liquid inlet communicating with the passage; a water-absorbent member accommodated in the passage and disposed between the liquid outlet and the liquid inlet.

In order to achieve the above-mentioned object, the present invention provides a humidifying device for a breathing mask. The humidifying device comprises: a body including a passage; a liquid discharger connected above the passage, the liquid discharger including a liquid outlet communicating with the passage; a liquid receiver connected below the passage, the liquid receiver including a liquid inlet communicating with the passage; and a water-absorbent member accommodated in the passage and disposed between the liquid outlet and the liquid inlet.

In order to achieve the above-mentioned object, the present invention provides a humidifying device for a breathing mask. The humidifying device comprises: a body including a passage; a water-absorbent member accommodated in the passage; and a liquid discharger and a liquid receiver respectively connected at two opposite ends of the water-absorbent member.

The present invention also has effects as follows.

First, the humidifying device is constituted by assembling simple parts with small size and light weight, and thereby the humidifying device of the present invention has a reduced size, so the humidifying device is small and is easy to carry.

Second, the humidifying device is constituted by assembling simple parts such as the body, the liquid discharger, the liquid receiver, and the water-absorbent member. Therefore, the humidifying device has advantages of being assembled, disassembled, and repaired conveniently.

Third, when the water-absorbent member is saturated with water or therapeutic liquid, superfluous water or therapeutic liquid drops into the liquid receiver through the liquid inlet, thereby preventing water or therapeutic liquid overflowing from the water-absorbent member from flowing into the breathing tube, thus enhancing safety in use of the humidifying device.

Fourth, the humidifying device of the present invention only heats the outlet side and is not required to heat the whole liquid discharger, thereby saving power consumption of the humidifying device.

DETAILED DESCRIPTION

Detailed descriptions and technical contents of the present invention are illustrated below in conjunction with the accompany drawings. However, it is to be understood that the descriptions and the accompany drawings disclosed herein are merely illustrative and exemplary and not intended to limit the scope of the present invention.

Figure 1:
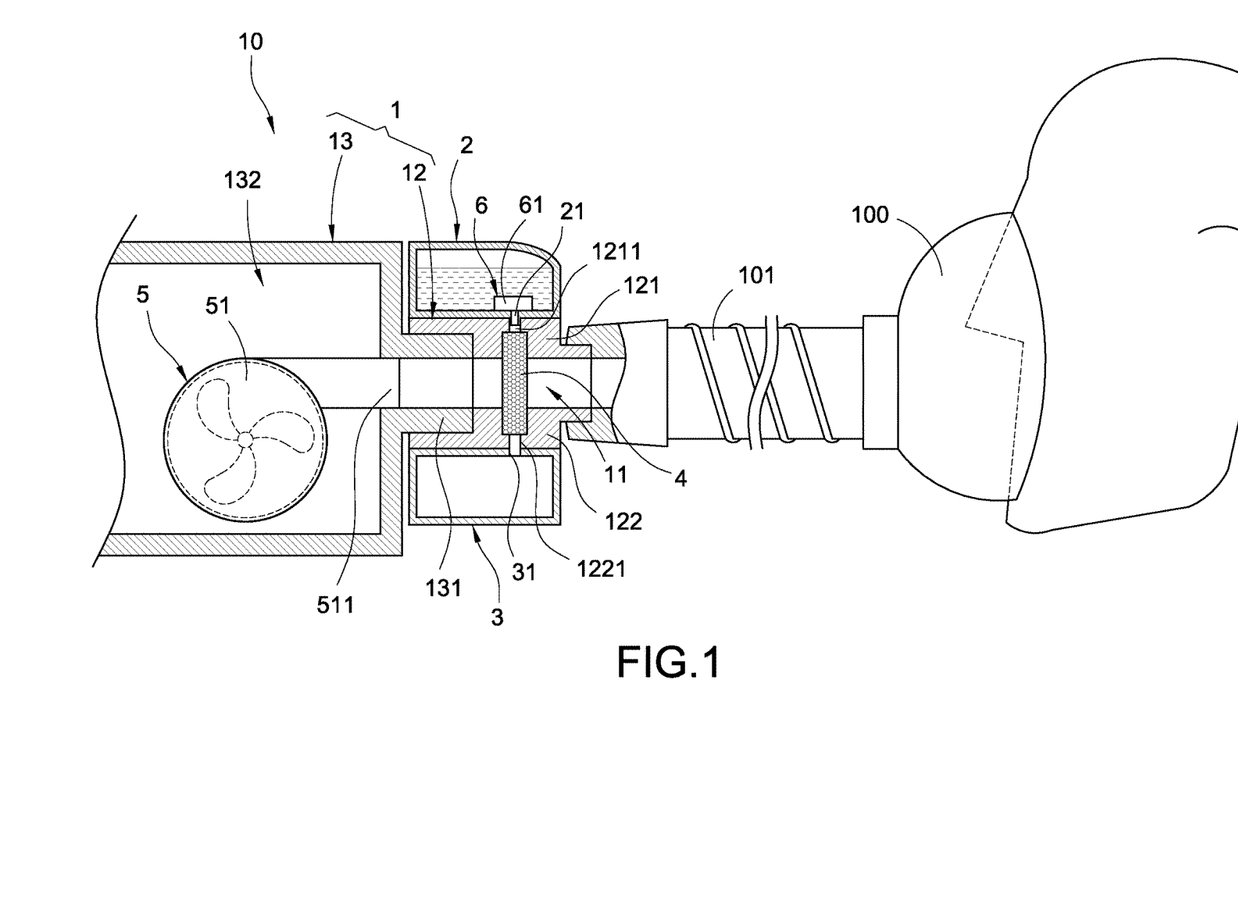
FIG. 1 is a cross-sectional view of a humidifying device according to a first embodiment of the present invention.
Figure 2:
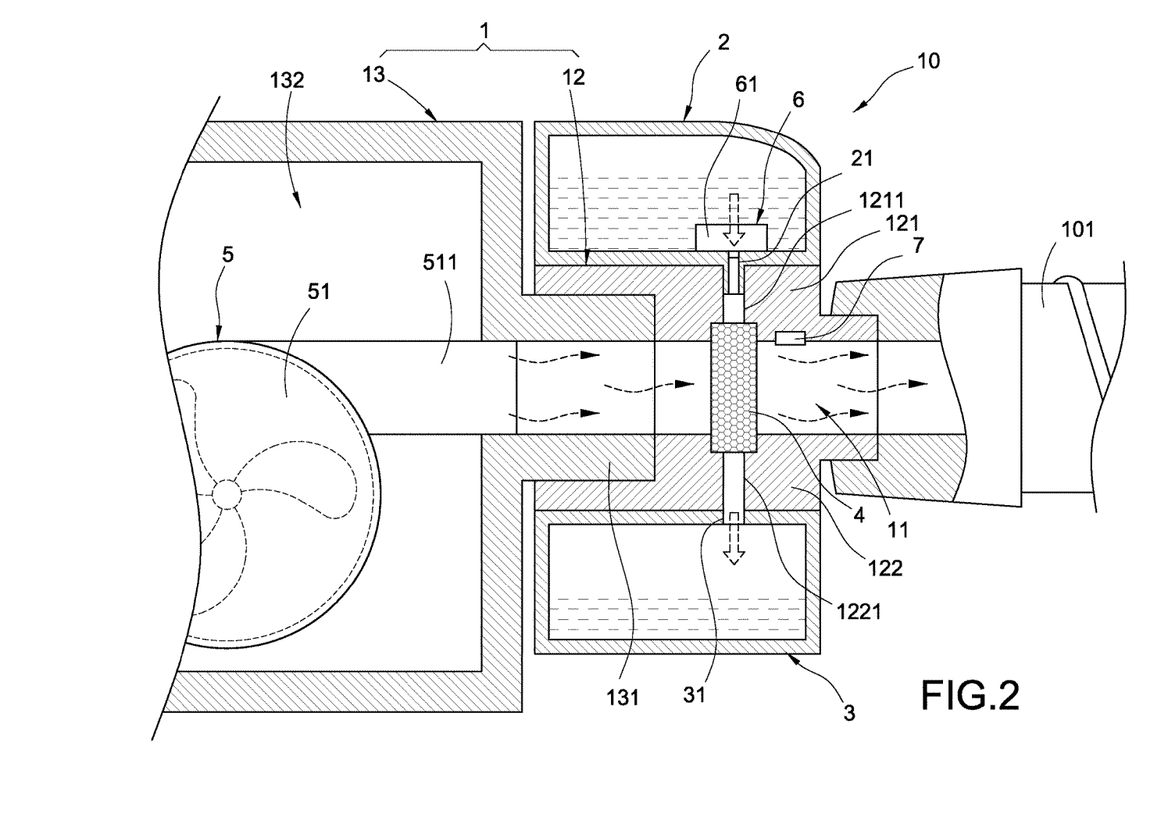
FIG. 2 is a use state view of the humidifying device according to the first embodiment of the present invention.

Please refer to FIGS. 1 and 2 which show a humidifying device for a breathing mask according to a first embodiment of the present invention. The breathing mask 100 including a breathing tube 101 assembled thereto. The humidifying device 10 comprises a body 1, a liquid discharger 2, a liquid receiver 3, and a water-absorbent member 4.

The body 1 includes a connecting tube 12. The connecting tube 12 is connected to the breathing tube 101. The connecting tube 12 includes a passage 11. The passage 11 is connected to the breathing tube 101. The body 1 comprises a connecting tube 12 and an assembly base 13. The connecting tube 12 is assembled between the breathing tube 101 and the assembly base 13, and the passage 11 is formed inside the connecting tube 12.

To be specific, the connecting tube 12 is a joint. According to a cross-sectional view of the connecting tube 12, the connecting tube 12 includes a top tube wall 121 and a bottom tube wall 122 disposed corresponding to each other. The top tube wall 121 includes a top through hole 1211 communicating with the passage 11. The bottom tube wall 122 includes a bottom through hole 1221 communicating with the passage 11. A joint 131 extends from one end of the assembly base 13. An accommodation space 132 is formed inside the assembly base 13. The joint 131 and the connecting tube 12 are assembled to each other.

The liquid discharger 2 is connected to the connecting tube 12. The liquid discharger 2 includes a liquid outlet 21 communicating with the passage 11. In detail, the liquid discharger 2 is fixed to the top tube wall 121. One end of the top through hole 1211 communicates with the liquid outlet 21, and the other end of the top through hole 1211 communicates with the passage 11.

The liquid receiver 3 is connected to the connecting tube and is disposed below the liquid discharger 2. The liquid receiver 3 includes a liquid inlet 31 communicating with the passage 11. In detail, the liquid receiver 3 is fixed to the bottom tube wall 122. One end of the bottom through hole 1221 communicates with the liquid inlet 31, and the other end of the bottom through hole 1221 communicates with the passage 11.

The water-absorbent member 4 consists of a filtering material. The water-absorbent member 4 is accommodated in the passage 11 and is disposed between the liquid outlet 21 and liquid inlet 31. In detail, one end of the water-absorbent member 4 is inserted in the top through hole 1211, and the other end of the water-absorbent member 4 is inserted in the bottom through hole 1221. According to the present embodiment, the water-absorbent member 4 consists of a filtering sponge; however, the present invention is not limited thereto.

The humidifying device 10 further comprises an airflow generator 5, and the airflow generator 5 is disposed corresponding to the water-absorbent member 4. According to the present embodiment, the airflow generator 5 is a blowing machine 51. The blowing machine 51 includes an air outlet 511. The blowing machine 51 is accommodated in the accommodation space 132, and the air outlet 511 is inserted in the joint 131.

Furthermore, the airflow generator 5 is not limited to the blowing machine 51. The airflow generator 5 can be a fan, a positive/negative-pressure air compressor, or other structure which can generates airflow.

The humidifying device 10 further includes a switch valve 6. The switch valve 6 is assembled to the liquid discharger 2. The switch valve 6 is a water-control solenoid valve 61. The water-control solenoid valve 61 is assembled at the liquid outlet 21 to adjust a flow amount of the discharged liquid/water.

The humidifying device 10 of the present invention further includes a sensor 7. The sensor 7 is disposed among the passage 11, the water-absorbent member 4, and the breathing tube 101. The sensor 7 is a humidity sensor. The humidity sensor 7 is used to generate a signal upon sensing humidity change and transmit the signal to an operation center (not illustrated), and thereby the operation center adjusts the flow amount of the liquid/water discharged from the water-control solenoid valve 61, so as to control the humidity of the air entering the breathing tube 101.

Referring to FIGS. 1 and 2, the humidifying device 10 of the present invention comprises: the connecting tube 12 connected to the breathing tube 101, the connecting tube 12 including the passage 11, the passage 11 being connected to the breathing tube 101; the liquid discharger 2 disposed in the connecting tube 12, the liquid discharger 2 including the liquid outlet 21 communicating with the passage 11; the liquid receiver 3 disposed in the connecting tube 12 and disposed below the liquid discharger 2, the liquid receiver 3 including the liquid inlet 31 communicating with the passage 11; the water-absorbent member 4 consisting of a filtering material, the water-absorbent member 4 being accommodated in the passage 11 and disposed between the liquid outlet 21 and the liquid inlet 31. Accordingly, the humidifying device 10 is constituted by simple parts assembled to one another, and therefore the humidifying device 10 has reduced size and low power consumption.

Please refer to FIG. 2 which illustrates a use state of the humidifying device 10. First, the liquid discharger 2 is filled with water or therapeutic liquid. The flow amount of the liquid discharged from the liquid discharger 2 is adjusted by the switch valve 6, so that the water or the therapeutic liquid stably drops to the water-absorbent member 4 through the liquid outlet 21. Then, the blowing machine 51 outputs airflow, and the airflow includes a large amount of moist vapor and flows into the breathing tube 101, thereby increasing the air humidity in the breathing tube 101.

Moreover, when the water-absorbent member 4 is saturated with water or therapeutic liquid, superfluous water or therapeutic liquid drops into the liquid receiver 3 through the liquid inlet 31, so the liquid receiver 3 receives the water or therapeutic liquid overflowing from the water-absorbent member 4, thereby preventing the water or therapeutic liquid overflowing from the water-absorbent member 4 from flowing into the breathing tube 101 to affect safety in respiration.

Compared to a conventional large-sized humidifying device, the humidifying device 10 of the present invention is constituted by assembling together small and light parts such as the body 1, the liquid discharger 2, the liquid receiver 3, the water-absorbent member 4, and the airflow generator 5. Thus, the humidifying device 10 has a reduced size as compared to the conventional humidifying device, thereby having features of being small and easy to carry.

Furthermore, the humidifying device 10 is constituted by assembling together simple parts including the body 1, the liquid discharger 2, the liquid receiver 3, the water-absorbent member 4, and the airflow generator 5. Therefore, the humidifying device 10 has advantages of being assembled, disassembled, and repaired conveniently.

Moreover, when the water-absorbent member 4 is saturated with water or therapeutic liquid, superfluous water or therapeutic liquid drops into the liquid receiver 3 through the liquid inlet 31, thereby preventing the water or therapeutic liquid overflowing from the water-absorbent member 4 from flowing into the breathing tube 101, thus enhancing the safety in using the humidifying device 10.

Figure 3:
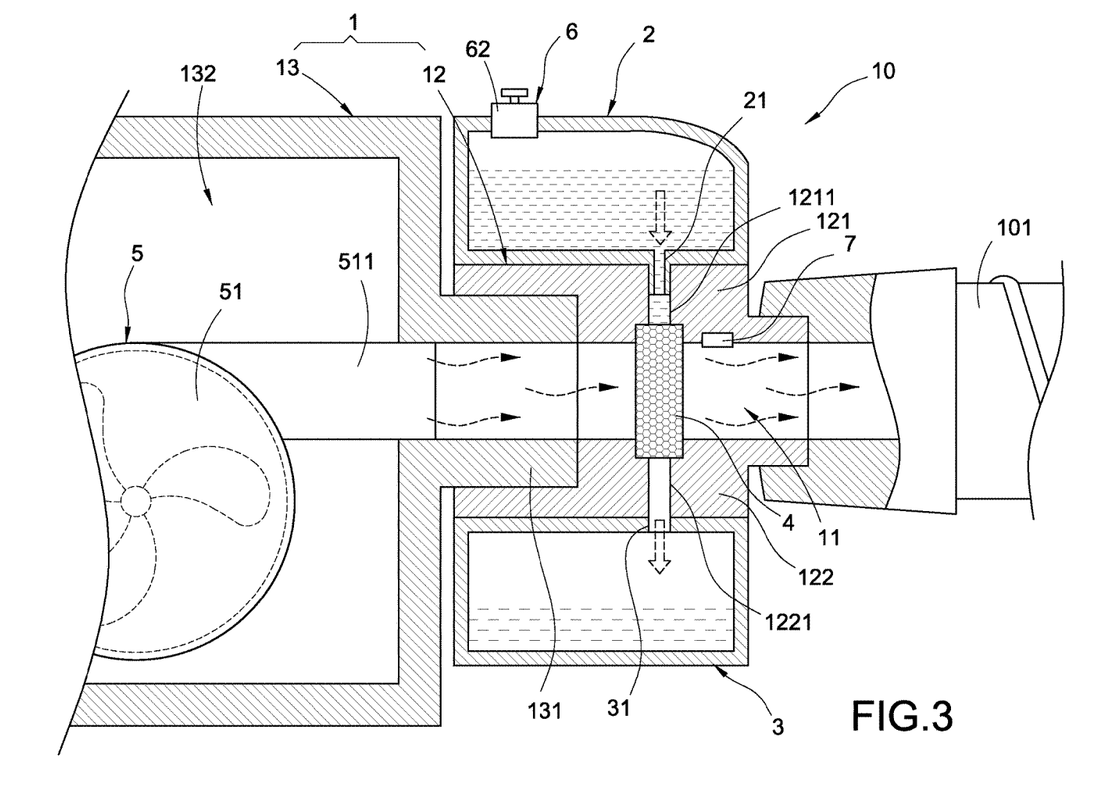
FIG. 3 is a use state view of the humidifying device according to a second embodiment of the present invention.

Please refer to FIG. 3 which illustrates the humidifying device 10 according to a second embodiment of the present invention. The second embodiment is similar to the first embodiment. The difference between the second embodiment and the first embodiment lies in that the switch valve 6 is an air vent valve 62.

In detail, the switch valve 6 can be a single-way or a two-way air vent valve 62 to permit entry of the outside air into the liquid discharger 2 and to drop the water or therapeutic liquid to the water-absorbent member 4, thereby achieving the same functions and effects as the first embodiment.

If the switch valve 6 is the single-way air vent valve 62, it can be disposed at any position in the liquid discharger 2. If the switch valve 6 is the two-way air vent valve 62, it has to be disposed at a top of the liquid discharger 2 to prevent the water or therapeutic liquid from flowing reversely.

Figure 4:
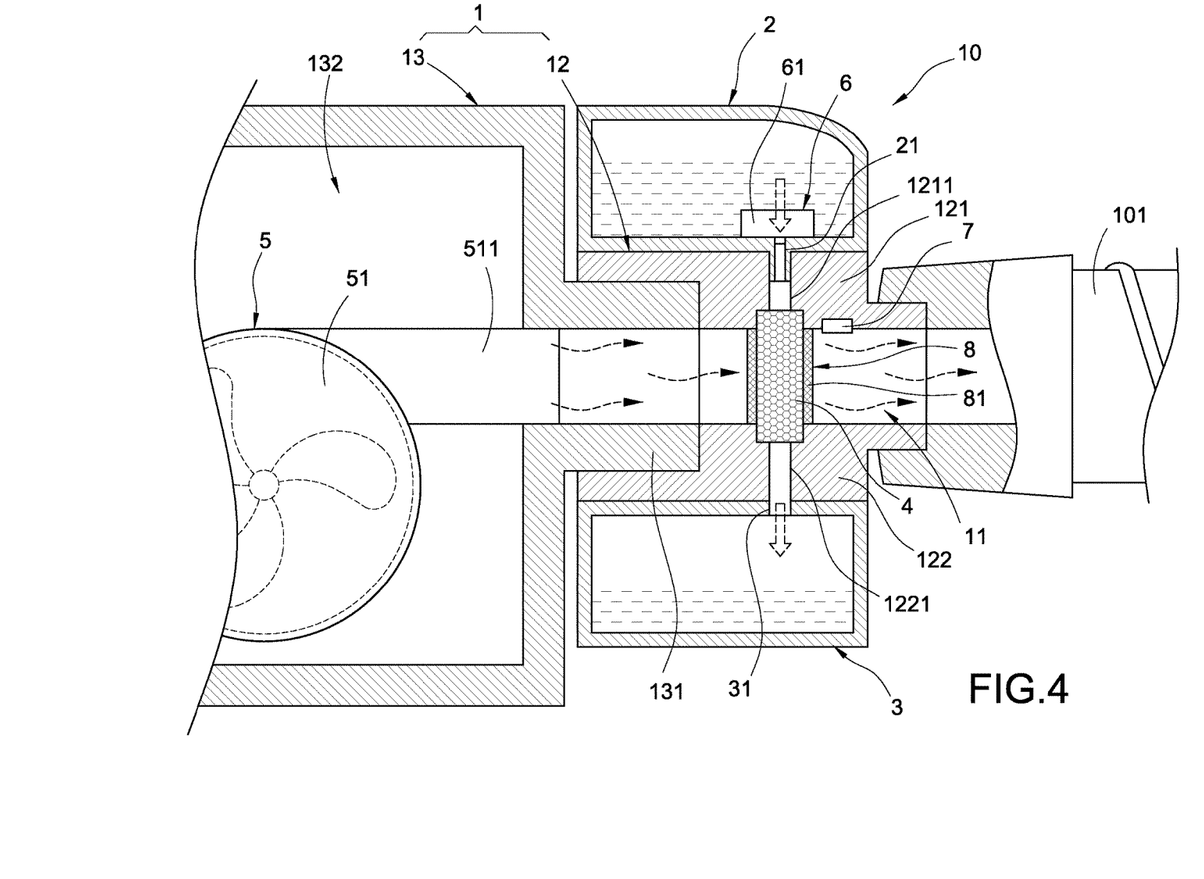
FIG. 4 is a use state view of the humidifying device according to a third embodiment of the present invention.

Please refer to FIG. 4 which illustrates the humidifying device 10 according to a third embodiment of the present invention. The third embodiment is similar to the first embodiment. The difference between the third embodiment and the first embodiment lies in that the humidifying device 10 further includes a heater 8 which is attached to the water-absorbent member 4.

In detail, the heater 8 is in a block shape, a plate shape, or a webbed shape. According to the present embodiment, the heater 8 is a heating web 81; however, the present invention is not limited thereto. The heating web 81 is attached to the water-absorbent member 4, so that the heating web 81 can heat the water-absorbent member 4. The blowing machine 51 outputs airflow. After the airflow enters the passage 11 and passes the wet and heated water-absorbent member 4, the airflow includes a large amount of warm moist vapor and flows into the breathing tube 101, so as to increase the air humidity and temperature in the breathing tube 101 and at the same time achieve the same functions and effects as the first embodiment.

Additionally, the conventional humidifying device usually heats a whole water tank and utilizes a fan to blow to the breathing tube 101 the heated vapor of the water or the therapeutic liquid. By contrast, the humidifying device 10 of the present invention only heats the outlet side of the water-absorbent member 4 and is not required to heat the whole liquid discharger 2, thereby reducing power consumption of the humidifying device 10.

Furthermore, the sensor 7 can be a temperature sensor. The sensor 7 is disposed among the passage 11, the water-absorbent member 4, and the breathing tube 101. The sensor 7 is used to generate a signal upon sensing temperature change in a space and to transmit the signal to the operation center (not illustrated). The operation center (not illustrated) adjusts the heating temperature of the heating web 81 upon receiving the signal, so as to control the temperature of the air entering the breathing tube 101.

Figure 5:
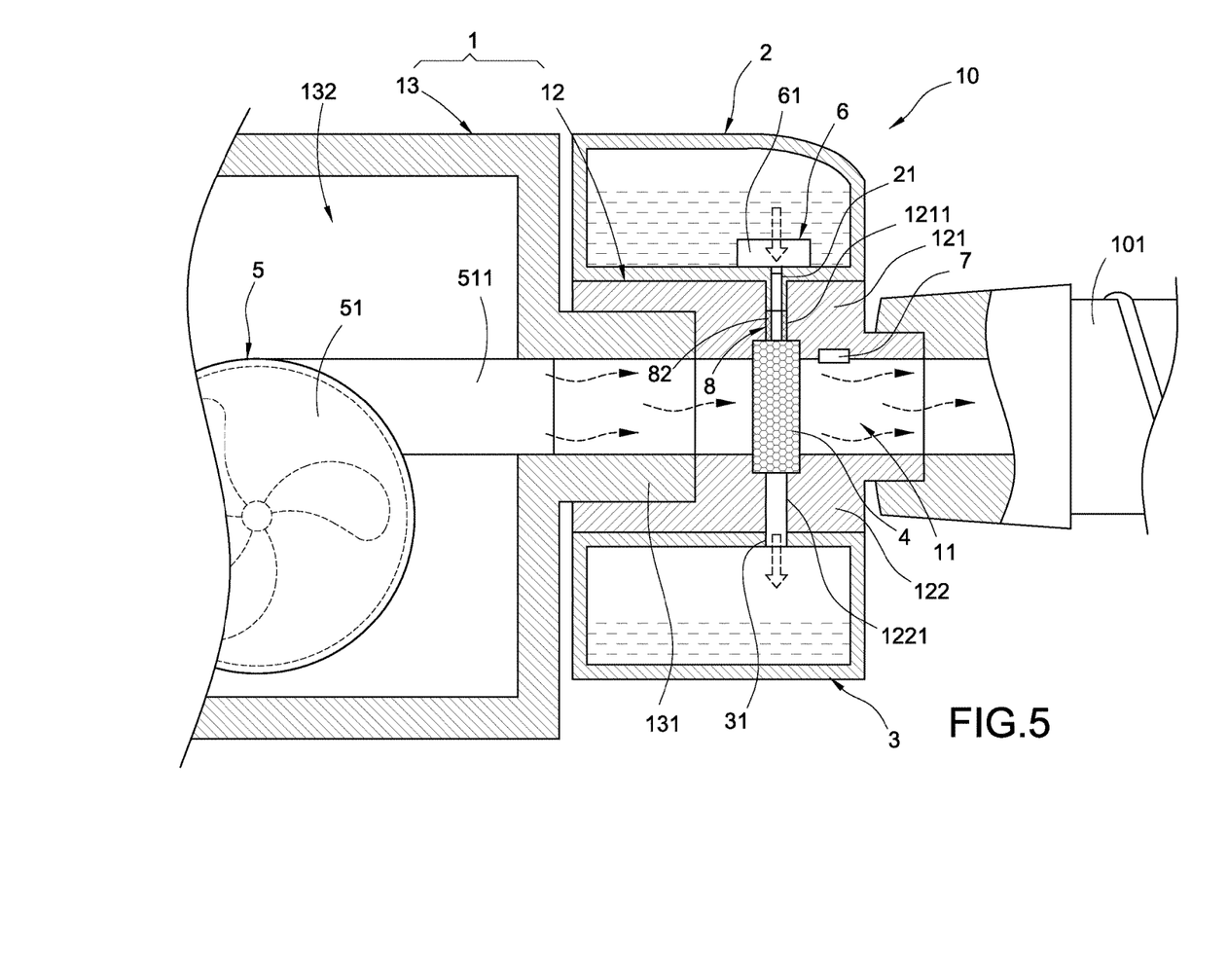
FIG. 5 is a use state view of the humidifying device according to a fourth embodiment of the present invention.

Please refer to FIG. 5 which illustrates a fourth embodiment of the humidifying device 10 of the present invention. The fourth embodiment is similar to the third embodiment. The difference between the fourth embodiment and the third embodiment lies in that the heater 8 is disposed corresponding to the liquid outlet 21.

Referring to FIG. 5, to be specific, the heater 8 is in a block shape, a plate shape, or a webbed shape. According to the present embodiment, the heater 8 is a heating block 82; however, the present invention is not limited thereto. The heating block 82 is disposed in the top through hole 1211, so that the water or therapeutic liquid is heated by the heating block 82 when the water of therapeutic liquid drops into the top through hole 1211 through the liquid inlet 31. Then, the heated water or therapeutic liquid is absorbed by the water-absorbent member 4. The blowing machine 51 outputs airflow, the airflow includes a large amount of warm moist vapor and flows into the breathing tube 101 after the airflow enters the passage 11 and passes the wet water-absorbent member 4, so as to increase the air humidity in the breathing tube 101 and at the same time achieve the same functions and effects as the third embodiment.

Besides, the conventional humidifying device usually heats the whole water tank and utilizes the fan to blow to the breathing tube 101 the heated vapor. By contrast, the humidifying device 10 of the present invention only heats the outlet side such as the top through hole 1211 and is not required to heat the whole liquid discharger 2, thereby reducing power consumption of the humidifying device 10.

In summary, the humidifying device for the breathing mask according to the present invention has neither been revealed by similar products nor put into public use, and the present invention completely meets the requirements of patentability, namely industrial applicability, novelty, and non-obviousness. Hence, a request to patent the present invention is filed based on the patent laws. Examination is kindly requested, and allowance of the present patent application is solicited to protect the rights of the inventor.

What is claimed is:

1. A humidifying device for a breathing mask, the breathing mask including a breathing tube assembled thereto, the humidifying device comprising:
    a connecting tube connected to the breathing tube, the connecting tube including a passage, the passage being connected to the breathing tube;
    a liquid discharger including a liquid outlet communicating with the passage;
    a liquid receiver including a liquid inlet communicating with the passage; and
    a water-absorbent member accommodated in the passage and disposed between the liquid outlet and the liquid inlet.

2. The humidifying device for the breathing mask of claim 1, further comprising a switch valve, the switch valve being assembled on the liquid discharger.

3. The humidifying device for the breathing mask of claim 2, wherein the switch valve is a water-control solenoid valve or an air vent valve.

4. The humidifying device for the breathing mask of claim 1, further comprising a sensor, the sensor being disposed among the passage, the water-absorbent member, and the breathing tube, the sensor being a humidity sensor.

5. The humidifying device for the breathing mask of claim 1, further comprising a heater, the heater being attached to the water-absorbent member.

6. The humidifying device for the breathing mask of claim 1, further comprising a heater, the heater being disposed corresponding to the liquid outlet.

7. The humidifying device for the breathing mask of claim 6, wherein the heater is disposed in a top through hole.

8. The humidifying device for the breathing mask of claim 5, wherein the heater is in a block shape, a plate shape, or a webbed shape.

9. A humidifying device for a breathing mask, the humidifying device comprising:
    a body including a passage;
    a liquid discharger connected above the body, the liquid discharger including a liquid outlet communicating with the passage;
    a liquid receiver connected below the body, the liquid receiver including a liquid inlet communicating with the passage; and
    a water-absorbent member accommodated in the passage and disposed between the liquid outlet and the liquid inlet.

10. The humidifying device for the breathing mask of claim 9, further comprising a switch valve, the switch valve being assembled on the liquid outlet.

11. The humidifying device for the breathing mask of claim 9, further comprising a switch valve, the switch valve being a water-control solenoid valve or an air vent valve.

12. The humidifying device for the breathing mask of claim 9, wherein the body includes a connecting tube and an assembly base, the connecting tube and the assembly base are assembled to each other, the passage is formed in the connecting tube, the connecting tube includes a top tube wall and a bottom tube wall disposed corresponding to each other, the liquid discharger is fixed to the top tube wall, the liquid receiver is fixed to the bottom tube wall, the top tube wall includes a top through hole communicating with the liquid outlet and the passage, the bottom tube wall includes a bottom through hole communicating with the liquid inlet and the passage, one end of the water-absorbent member is inserted in the top through hole, and an opposite end of the water-absorbent member is inserted in the bottom through hole.

13. The humidifying device for the breathing mask of claim 9, further comprising a sensor, the sensor being disposed between the passage and the water-absorbent member, the sensor being a humidity sensor or a temperature sensor.

14. The humidifying device for the breathing mask of claim 9, further comprising a heater, the heater being attached to the water-absorbent member.

15. The humidifying device for the breathing mask of claim 9, further comprising a heater, the heater being disposed corresponding to the liquid outlet.

16. The humidifying device for the breathing mask of claim 15, wherein the heater is disposed in a top through hole.

17. The humidifying device for the breathing mask of claim 15, wherein the heater is in a block shape, a plate shape, or a webbed shape.

18. A humidifying device for a breathing mask, the humidifying device comprising:
   a connecting tube including a passage;
   a water-absorbent member accommodated in the passage; and
   a liquid discharger and a liquid receiver respectively connected at two opposite ends of the water-absorbent member.

19. The humidifying device for the breathing mask of claim 18, further comprising a switch valve, the switch valve being assembled on the liquid discharger.

20. The humidifying device for the breathing mask of claim 18, wherein the connecting tube and an assembly base are assembled to each other, the passage is formed inside the connecting tube, the connecting tube includes a top tube wall and a bottom tube wall disposed corresponding to each other, the liquid discharger is fixed to the top tube wall, the liquid receiver is fixed to the bottom tube wall, the top tube wall includes a top through hole communicating with the liquid outlet and the passage, the bottom tube wall includes a bottom through hole communicating with the liquid inlet and the passage, one end of the water-absorbent member is inserted in the top through hole, and the other end of the water-absorbent member is inserted in the bottom through hole.

21. The humidifying device for the breathing mask of claim 18, further comprising a sensor, the sensor being disposed among the passage and the water-absorbent member, the sensor being a humidity sensor or a temperature sensor.

22. The humidifying device for the breathing mask of claim 18, further comprising a heater, the heater being attached to the water-absorbent member.

23. The humidifying device for the breathing mask of claim 18, further comprising a heater, the heater being disposed corresponding to the liquid outlet.

* * * * *